United States Patent
Ding

(10) Patent No.: US 9,944,241 B2
(45) Date of Patent: *Apr. 17, 2018

(54) VEHICLE FINGERPRINT BOOKMARK

(71) Applicant: THUNDER POWER NEW ENERGY VEHICLE DEVELOPMENT COMPANY LIMITED, Central (HK)

(72) Inventor: Jia-Wei Ding, Taipei (TW)

(73) Assignee: THUNDER POWER NEW ENERGY VEHICLE DEVELOPMENT COMPANY LIMITED, Central (HK)

( * ) Notice: Subject to any disclaimer, the term of this patent is extended or adjusted under 35 U.S.C. 154(b) by 0 days.

This patent is subject to a terminal disclaimer.

(21) Appl. No.: 15/489,393

(22) Filed: Apr. 17, 2017

(65) Prior Publication Data
US 2017/0217391 A1  Aug. 3, 2017

Related U.S. Application Data

(60) Continuation of application No. 15/228,228, filed on Aug. 4, 2016, now Pat. No. 9,659,207, which is a
(Continued)

(51) Int. Cl.
*B60R 16/037* (2006.01)
*G06K 9/00* (2006.01)
(Continued)

(52) U.S. Cl.
CPC .............. *B60R 16/037* (2013.01); *G01L 1/26* (2013.01); *G01L 5/22* (2013.01);
(Continued)

(58) Field of Classification Search
CPC ......... G01L 1/26; G01L 5/22; G06K 9/00087; G06K 9/00013; G06F 17/30247; B60R 16/037
(Continued)

(56) References Cited

U.S. PATENT DOCUMENTS 6,100,811 A    8/2000 Hsu et al.
6,282,475 B1 * 8/2001 Washington ............ B60R 25/04
                                                       296/65.16
(Continued)

FOREIGN PATENT DOCUMENTS

BE    1 016 037 A6    1/2006
IN    3895MUM2014 A   10/2015

OTHER PUBLICATIONS

U.S. Appl. No. 14/940,161, filed Nov. 13, 2015, Non-Final Office Action dated Oct. 12, 2016, all pages.
(Continued)

*Primary Examiner* — Feng Niu
*Assistant Examiner* — Geoffrey E Summers
(74) *Attorney, Agent, or Firm* — Kilpatrick Townsend & Stockton LLP

(57) ABSTRACT

Provided in the present disclosure is a fingerprint bookmark system which may be implemented in a vehicle with one or more configurable interior settings. The fingerprint bookmark system may contain a scanner which may be configured to record a fingerprint from a vehicle occupant such that a fingerprint image showing the fingerprint and a duration data for the fingerprint image are recorded by the scanner. The system may contain one or more processors which may be configured to compare the duration data associated with the fingerprint image with a duration threshold. The one or more processors may be configured to initiate a search to obtain a bookmark for the fingerprint shown in the fingerprint image when the duration data is less than the duration threshold. The one or more processors may be further configured to create a new bookmark when the duration data exceeds the duration threshold.

5 Claims, 7 Drawing Sheets

Related U.S. Application Data division of application No. 14/967,397, filed on Dec. 14, 2015, now Pat. No. 9,639,620, which is a continuation of application No. 14/940,161, filed on Nov. 13, 2015.

(51) Int. Cl.
  *G06F 17/30*   (2006.01)
  *G01L 5/22*   (2006.01)
  *G01L 1/26*   (2006.01)

(52) U.S. Cl.
  CPC ... *G06F 17/30247* (2013.01); *G06K 9/00013* (2013.01); *G06K 9/00087* (2013.01)

(58) Field of Classification Search
  USPC .................................................. 382/104, 124
  See application file for complete search history.

(56) References Cited

U.S. PATENT DOCUMENTS

| | | | |
|---|---|---|---|
| 6,812,942 B2 | 11/2004 | Ribak | |
| 7,721,227 B2* | 5/2010 | Ronkainen | .......... G06F 3/04895 715/702 |
| 8,831,557 B2 | 9/2014 | Jung et al. | |
| 9,639,620 B1 | 5/2017 | Ding | |
| 9,659,207 B1 | 5/2017 | Ding | |
| 9,701,202 B2 | 7/2017 | Ding | |
| 9,830,492 B2 | 11/2017 | Ding | |
| 2002/0099784 A1 | 7/2002 | Tran | |
| 2006/0087405 A1 | 4/2006 | Koike et al. | |
| 2006/0284853 A1 | 12/2006 | Shapiro | |
| 2008/0166028 A1* | 7/2008 | Turek | ................... G06K 9/0002 382/124 |
| 2008/0223926 A1 | 8/2008 | Miller et al. | |
| 2011/0115606 A1 | 5/2011 | Fu et al. | |
| 2011/0207423 A1 | 8/2011 | Tarte | |
| 2013/0324089 A1 | 12/2013 | Kim et al. | |
| 2014/0156149 A1* | 6/2014 | Feit | ....................... B60R 25/252 701/49 |
| 2014/0309862 A1* | 10/2014 | Ricci | ..................... G01C 21/00 701/36 |
| 2014/0309864 A1 | 10/2014 | Ricci | |
| 2015/0135108 A1 | 5/2015 | Pope et al. | |
| 2016/0350578 A1 | 12/2016 | Chang | |
| 2017/0136879 A1 | 5/2017 | Ding | |

OTHER PUBLICATIONS

U.S. Appl. No. 14/967,397, filed Dec. 14, 2015, Final Office Action dated Oct. 12, 2016, all pages.
U.S. Appl. No. 14/967,397, filed Dec. 14, 2015, Non-Final Office Action dated Jul. 13, 2016, all pages.
U.S. Appl. No. 15/228,228, filed Aug. 4, 2016, Non-Final Office Action dated Oct. 4, 2016, all pages.
U.S. Appl. No. 15/228,228, filed Aug. 4, 2016, Notice of Allowance dated Jan. 31, 2017, all pages.
U.S. Appl. No. 15/479,038, filed Apr. 4, 2017, Notice of Allowance dated Aug. 10, 2017, all pages.
U.S. Appl. No. 15/600,293, filed May 19, 2017, all pages.
European Search Report for EP 16194292 dated Apr. 5, 2017, 11 pages.
U.S. Appl. No. 15/600,293, filed May 19, 2017, Final Rejection dated Oct. 12, 2017, all pages.
U.S. Appl. No. 15/600,293, filed May 19, 2017, Notice of Allowance dated Dec. 1, 2017, all pages.
U.S. Appl. No. 15/794,295, filed Oct. 26, 2017, Non-Final Rejection dated Dec. 20, 2017, all pages.

* cited by examiner

VEHICLE FINGERPRINT BOOKMARK

RELATED APPLICATIONS

The present application is a continuation of U.S. Nonprovisional application Ser. No. 15/228,228, filed Aug. 4, 2016, which is a divisional of U.S. Nonprovisional application Ser. No. 14/967,397, filed Dec. 14, 2015, which is a continuation of U.S. Nonprovisional application Ser. No. 14/940,161, filed Nov. 13, 2015, the disclosures of which are hereby incorporated by reference in their entirety for all purposes.

BACKGROUND

Vehicle manufacturers have added a number of new features to vehicle interior cabins over the last few decades to make their operation more comfortable and efficient. These features include: modern A/C and heating systems, GPS, satelite radio, back-up cameras, side cameras, seat warmers, power seat adjusters, power sun roof, power windows, automatic parking, digital displays on dashboard and control panel, etc. Many of these features can be personalized for different users, such as seat position and digital display settings. In general, different users of a vehicle need to reconfigure each feature upon entry. This can be both time-consuming and inefficient. The present disclosure solves this problem by providing a quick, efficient way to "bookmark" the interior settings of a vehicle by associating a user's fingerprint with the user's previous adjustment of the interior settings.

BRIEF SUMMARY

Provided in the present disclosure is a fingerprint bookmark system which may be implemented in a vehicle with one or more configurable interior settings. The fingerprint bookmark system may contain a scanner which may be configured to record a fingerprint from a vehicle occupant such that a fingerprint image showing the fingerprint and a duration data for the fingerprint image are recorded by the scanner. The duration data may indicate a time value associated with the fingerprint image. The system may also contain one or more processors which may be configured to compare the duration data associated with the fingerprint image with a duration threshold. The one or more processors may additionally be configured to initiate a search to obtain a bookmark for the fingerprint shown in the fingerprint image when the duration data is less than the duration threshold. The one or more processors may be further configured to create a new bookmark for the fingerprint shown in the fingerprint image when the duration data exceeds the duration threshold. The new bookmark may contain at least one instruction that is different from the instructions contained in the old bookmark.

The one or more processors of the fingerprint bookmark system may initiate a search to obtain a bookmark. This initiation of a search may include the generating of a search request for execution by a server, where the search request may indicate the fingerprint image. The initiation of a search may also include the receiving of a bookmark from the server after the server finds a match between the fingerprint image and a stored fingerprint image. The stored fingerprint image may be associated with the bookmark.

The duration threshold of the fingerprint bookmark system may be three seconds. The one or more processors may be located in the vehicle, in the scanner, or in the server. The one or more processors may be further configured to perform no action when a bookmark is not found and the duration data is less than the duration threshold. The fingerprint image may be an image of multiple fingerprints. The configurable interior settings of a vehicle may include any of the following: seat adjustment, mirror adjustment, air temperature, seat temperature, radio, GPS, and dashboard arrangement.

The fingerprint bookmark system may contain a scanner which may be configured to record a fingerprint from a vehicle occupant such that a fingerprint image showing the fingerprint and a firmness data for the fingerprint image are recorded by the scanner. The firmness data may indicate a firmness value associated with the fingerprint image. The system also contain one or more processors which may be configured to compare the firmness data associated with the fingerprint image with a firmness threshold. The one or more processors may additionally be configured to initiate a search to obtain a bookmark for the fingerprint shown in the fingerprint image when the firmness data is less than the firmness threshold. The one or more processors may be further configured to create a new bookmark for the fingerprint shown in the fingerprint image when the firmness data exceeds the firmness threshold. The new bookmark may contain at least one instruction that is different from the instructions contained in the old bookmark. The one or more processors may be further configured to perform no action when the bookmark is not found and the firmness data is below the firmness threshold.

Additionally provided in the present disclosure is a method for configuring interior settings of a vehicle. The method may include the step of recording, by a scanner, a fingerprint from a vehicle occupant such that a fingerprint image showing the fingerprint and a duration data for the fingerprint image are recorded by the scanner. The duration data may indicate a time value associated with the fingerprint image. The method may include the step of outputting, by the scanner, the fingerprint image to a server. The method may also include the step of comparing, by one or more processors, the duration data associated with the fingerprint image with a duration threshold. The method may additionally include the step of initiating a search when the duration data is less than the duration threshold to obtain a bookmark for the fingerprint shown in the fingerprint image. The method may further include the step of creating a new bookmark when the duration data exceeds the duration threshold for the fingerprint shown in the fingerprint image.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention claimed. The detailed description and the specific examples, however, indicate only preferred embodiments of the invention. Various changes and modifications within the spirit and scope of the invention will become apparent to those skilled in the art from this detailed description.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention.

No attempt is made to show structural details of the invention in more detail than may be necessary for a fundamental understanding of the invention and various ways in which it may be practiced.

Figure 1:
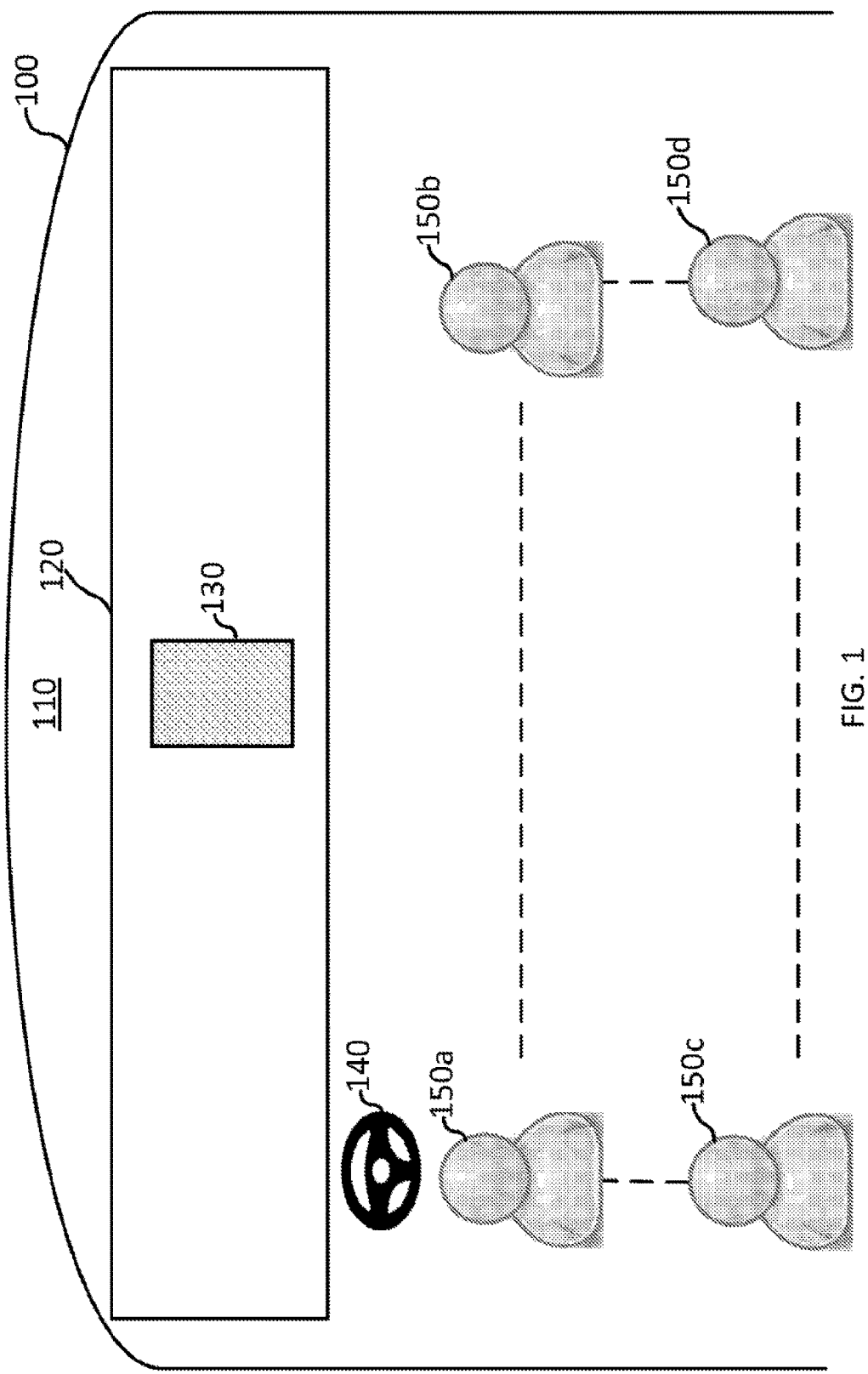
FIG. 1 shows a fingerprint bookmark system inside a transportation apparatus, according to an exemplary embodiment of the present disclosure.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

Various example embodiments of the present disclosure will be described below with reference to the drawings constituting a part of the description. It should be understood that, although terms representing directions are used in the present disclosure, such as "front", "rear", "upper", "lower", "left", "right", and the like, for describing various exemplary structural parts and elements of the present disclosure, these terms are used herein only for the purpose of convenience of explanation and are determined based on the exemplary orientations shown in the drawings. Since the embodiments disclosed by the present disclosure can be arranged according to different directions, these terms representing directions are merely used for illustration and should not be regarded as limiting. Wherever possible, the same or similar reference marks used in the present disclosure refer to the same components.

Unless defined otherwise, all technical terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Described herein, are embodiments for a fingerprint bookmark system that may be employed in a vehicle. The present disclosure solves the problem in the automobile industry in which different drivers of the same vehicles must reconfigure a wide range of interior settings in a vehicle upon each entry. The fingerprint bookmark system provides a quick, efficient way to "bookmark" the interior settings of a vehicle by associating a user's fingerprint with the user's previous adjustment of the interior settings. The system may quickly differentiate between a "short touch" and a "long touch", the former being associated with implementing a previously recorded bookmark and the latter being associated with recording a new bookmark.

FIG. 1 generally illustrates an exemplary embodiment of a fingerprint bookmark system 130 on a dashboard 120 in a transportation apparatus 100. Transportation apparatus 100 may include any apparatus that moves in distance. Examples of transportation apparatus 100 may include a vehicle such as a car, a bus, a train, a truck, a tram, or any other type of vehicle; may include a vessel such as a boat, a ship, a barge, a ferry or any other type of watercraft; may include an aircraft such as an airplane, a spaceship, or any other type of aircraft; or may include any other transportation apparatus. In one example, transportation apparatus 100 is an electrical automobile. As shown, transportation apparatus 100 may include a cabin 110 with a volume.

As shown in FIG. 1, transportation apparatus 100 may comprise one or more steering wheels 140 in cabin 110. Although only one steering wheel 140 is shown in FIG. 1, this is not intended to be limiting. In some examples, transportation apparatus 100 may include more than one steering wheel 140. For example, it is contemplated that transportation apparatus 100 may be an aircraft that comprises at least a main steering wheel 140 for the main pilot and at least a secondary steering wheel 140 for a co-polit.

As also shown in FIG. 1, one or more users 150 may be arranged to occupy their corresponding positions in cabin 110. Users 150 may include one or more drivers that control the movement or navigation of transportation apparatus 100, one or more passengers, and/or any other type of users 150. In this example, user 150a is a driver that controls the driving of transportation apparatus 100, while other users 150, e.g., users 150b-d, are passengers. As still shown, there may be multiple rows of users 150 within cabin 110 of transportation apparatus 100.

In some embodiments, fingerprint bookmark system 130 can be accessed by any one of users 150. In some embodiments, fingerprint bookmark system 130 does not necessarily need to be located on dashboard 120, but may be located at any location within transportation apparatus 100, including a location on steering wheel 140. Furthermore, fingerprint bookmark system 130 can be used to adjust interior settings for any one of users 150. For example, user 150a may use fingerprint bookmark system 130 to adjust certain interior settings for user 150d, e.g., seat temperature, seat adjustment, etc. Similarly, user 150b may use vehicle interior control 130 to adjust certain interior settings for all users 150, e.g., air temperature.

Figure 2:
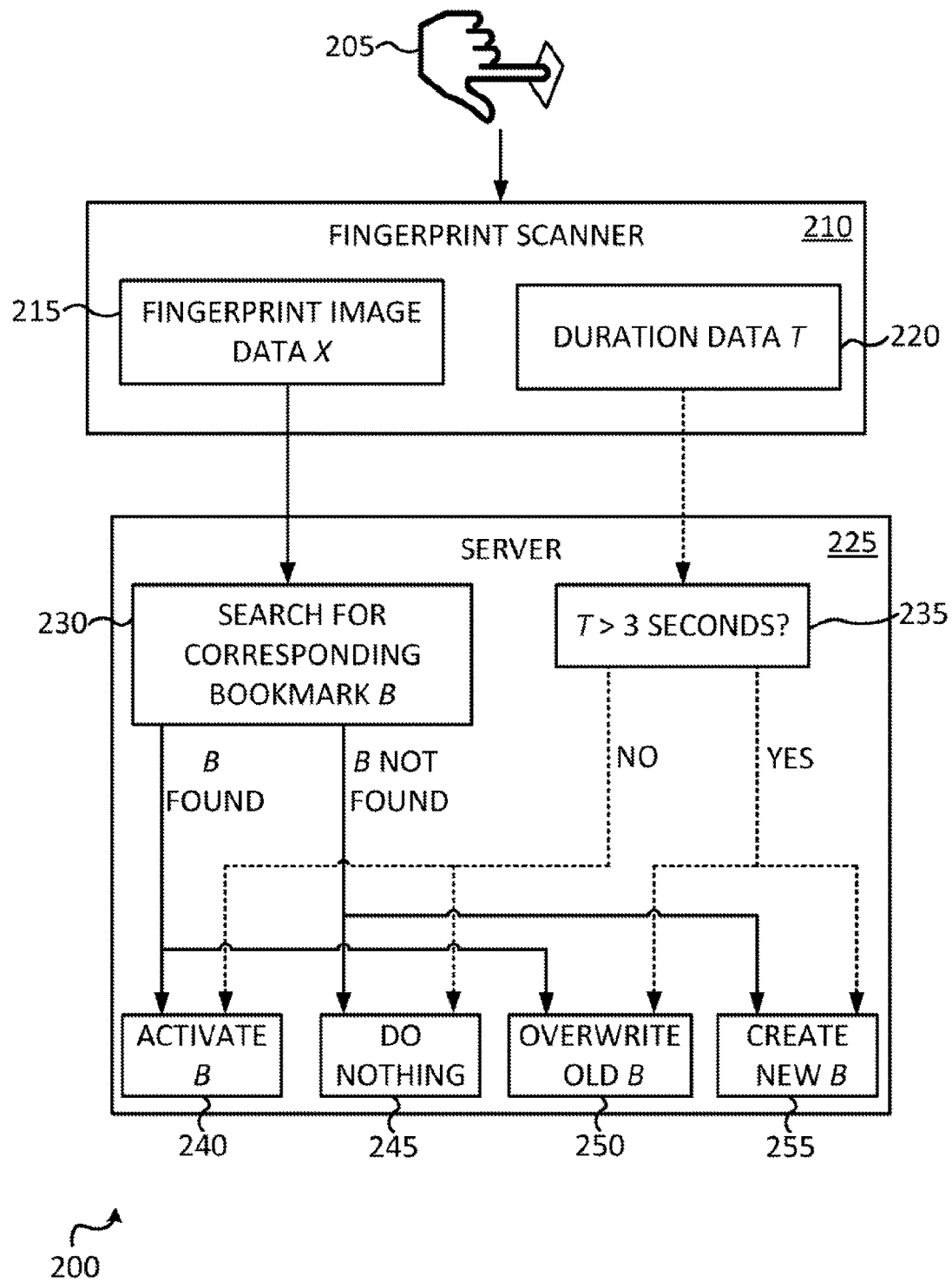
FIG. 2 shows a fingerprint bookmark system that captures duration data, according to an exemplary embodiment of the present disclosure.

FIG. 2 shows a fingerprint bookmark system 200 that captures duration data, according to an exemplary embodiment of the present disclosure. In some embodiments, a fingerprint scanner 210 records a fingerprint image data 215 from a user input 205. Fingerprint scanner 210 may be any one of a wide number of available fingerprint scanning technologies. For example, fingerprint scanner 210 may be a an optical sensor, a capacitive sensor, an ultrasound sensor, or a thermal sensor, among others. In some embodiments, fingerprint scanner 210 may be a capacitive sensor that determines each pixel value of an image based on the capacitance measured at each pixel location, which varies due to the different dielectric constants of skin ridges compared to a valleys. In some embodiments, fingerprint scanner 210 may employ a high frequency ultrasound or optical sensor that receives a varying signal based on the change in light reflectance related to the skin ridges. In some embodiments, finger print scanner 210 is a thermal scanner that measures the difference in temperature of different pixel areas, with high temperature areas corresponding to skin ridges and low temperature areas corresponding to valleys. In some embodiments, user input 205 may be placed directly on scanner 210, making physical contact with the surface of scanner 210. In some embodiments, user input 205 may be at a distance from scanner 210 when a recording is made.

In some embodiments, fingerprint image data 215 may be an image file. The image file may be compressed or uncompressed, and may be any one of several digital image file types, such as TIFF, JPEG, GIF, PNG, BMP, etc. In some embodiments, fingerprint image data 215 may not be an image file type, but may be a data representation of fingerprint topography. For example, while a fingerprint usually appears as a series of dark lines that represent ridges of the skin, fingerprint image data 215 may be an integer representing the number of ridges of the skin. Furthermore, fingerprint image data 215 may be an integer representing the number of crossovers, ridge bifurcations, ridge endings, islands, or pores that appear on a finger of user input 205. Furthermore, fingerprint image data 215 may be any digital representation of any feature of a fingerprint.

In some embodiments, user input 205 is not a single finger but one or more fingers of the same hand or of different hands. In some embodiments, user input 205 is not limited to a vehicle occupant's finger, but may include any one of several biometrics, such as facial recognition, palm print, iris scan, voice recognition, DNA, etc.

In some embodiments, fingerprint scanner 210 also records a duration data 220. Duration data 220 may indicate a time value associated with how long user input 205 is in direct physical contact with fingerprint scanner 210. For example, if fingerprint scanner 210 is an optical sensor and a vehicle occupant places a finger in direct contact with the scanner for 5 seconds, then duration data 220 may be equal to 5 seconds. In some embodiments, duration data 220 is not just a single numerical value but may be a set of numerical values representing present and past durations or durations of different fingers that are placed on fingerprint scanner 210 simultaneously.

In some embodiments, fingerprint image data 215 and duration data 220 are sent to a server 225. In some embodiments, server 225 is located outside the vehicle. In other embodiments, server 225 is located inside the vehicle, and behaves similar to a local storage device.

In some embodiments of the present disclosure, a set of fingerprint images and their corresponding bookmarks are stored within server 225. The stored bookmarks each contain one or more instructions for configuring interiors setting of a vehicle. Interior settings of a vehicle that may be configured by fingerprint bookmark system 200 include: A/C and heating settings, GPS, satellite radio, back-up cameras, side cameras, seat warmers, power seat adjusters, power sun roof, power windows, automatic parking, digital displays on dashboard and control panel, etc. For example, one bookmark may contain instructions to set the air temperature to 70 degrees Fahrenheit and the radio station to 96.3 FM. As another example, one bookmark may contain instructions to set the digital display on the dashboard to show the GPS display on the right side of the dashboard and the radio display on the left side, while another bookmark may contain instructions to display the opposite. As another example, one bookmark may contain instructions to set the driver's seat in a certain position, while another bookmark may contain instructions to set the passenger's seat in a certain position. In some embodiments, each stored fingerprint image within server 225 is associated with a different bookmark. In other embodiments, different stored fingerprint images within server 225 are associated with the same bookmark. For example, different vehicle occupants may prefer similar interior settings, such as radio station, digital display configuration, etc. It is easy to see the wide range of embodiments that are available through the present disclosure.

In some embodiments, at operation 230 server 225 may perform a search in which it is determined whether there is a stored fingerprint image within server 225 that matches fingerprint image data 215. The search at operation 230 need not necessarily be performed within server 225. Operation 230 may be performed by a processor located inside server 225, inside fingerprint scanner 210, inside the vehicle, or outside the vehicle. Operation 230 may performed according to any one of several available fingerprint matching techniques, such as minutiae-based matching techniques, which examine specific features of fingerprint topography, or pattern matching techniques, which compare two images to determine how similar they are.

In some embodiments, at operation 235 server 225 makes a determination as to whether duration data 220 exceeds some duration threshold. The duration threshold may be set to any time value, such as 3 seconds, 5 seconds, or 10 seconds. When duration data 220 is less than the duration threshold, it may be determined that user input 205 from the vehicle occupant was a "short touch". Conversely, when duration data 220 exceeds the duration threshold, it may be determined that user input 205 from the vehicle occupant was a "long touch". When duration data 220 is equal to the duration threshold, it may be a "short touch" or a "long touch", depending on the embodiment. The determination at operation 235 need not necessarily be performed within server 225. Operation 235 may be performed by a processor located inside server 225, inside fingerprint scanner 210, inside the vehicle, or outside the vehicle. Operation 235 may be performed in software, or in hardware such as using a comparator circuit.

In some embodiments, fingerprint bookmark system 200 makes a determination as to which of several operations to perform. These operations include, but are not limited to: a first operation 240 to activate a found bookmark when search 230 finds a matching bookmark and duration data 220 is less than the duration threshold, a second operation 245 to do nothing when search 230 does not find a matching bookmark and duration data 220 is less than the duration threshold, a third operation 250 to overwrite the found bookmark with a new bookmark comprising the vehicle's current interior settings when search 230 finds a matching bookmark and duration data 220 exceeds the duration threshold, and a fourth operation 255 to create a new bookmark comprising the vehicle's current interior settings when search 230 does not find a matching bookmark and duration data 220 exceeds the duration threshold.

Fingerprint bookmark system 200 need not necessarily determine which of these four operations to perform within server 225. The determination may be made by a processor located inside server 225, inside fingerprint scanner 210, inside the vehicle, or outside the vehicle. The determination may be performed in software or in hardware. Similarly, operations 240, 245, 250, and 255 may be initiated by a processor located inside server 225, inside fingerprint scanner 210, inside the vehicle, or outside the vehicle. Eventually, operations 240, 245, 250, and 255 may be communicated to the one or more vehicle interior settings to which a bookmark corresponds. For example, where a vehicle occupant indicates via user input 205 that he/she desires to activate a previously created bookmark to configure a satellite radio display on the dashboard, he/she may touch fingerprint scanner 210 for 1 second, which may be less than a duration threshold of 4 seconds, and may result in operation 240 being performed to send a signal from a server to the vehicle and subsequently to the digital display for the dashboard, indicating that the satellite radio be displayed according to the previously created bookmark.

As another example, a vehicle occupant may purchase a new vehicle with fingerprint bookmark system 200. Upon entry, the vehicle occupant may adjust the rear view mirror and side mirrors to his specifications and subsequently press fingerprint scanner 210 for 5 seconds, which may exceed a duration threshold of 2.5 seconds. Fingerprint image data 215 of the vehicle occupant's finger may be transmitted outside the vehicle to server 225 which may perform a search 230 for a corresponding bookmark with a matching stored fingerprint image. Search 230 may not find a corresponding bookmark due to vehicle occupant's first use of fingerprint bookmark system 200, causing a signal to be transmitted back to the vehicle indicating a corresponding bookmark was not found. Fingerprint bookmark system 200 may perform operation 255 to create a new bookmark comprising the vehicle's current interior settings which may include the current position of the rear view mirror and side mirrors. The newly created bookmark may be transmitted from inside the vehicle to outside the vehicle to server 225 to be stored for later retrieval.

Figure 3:
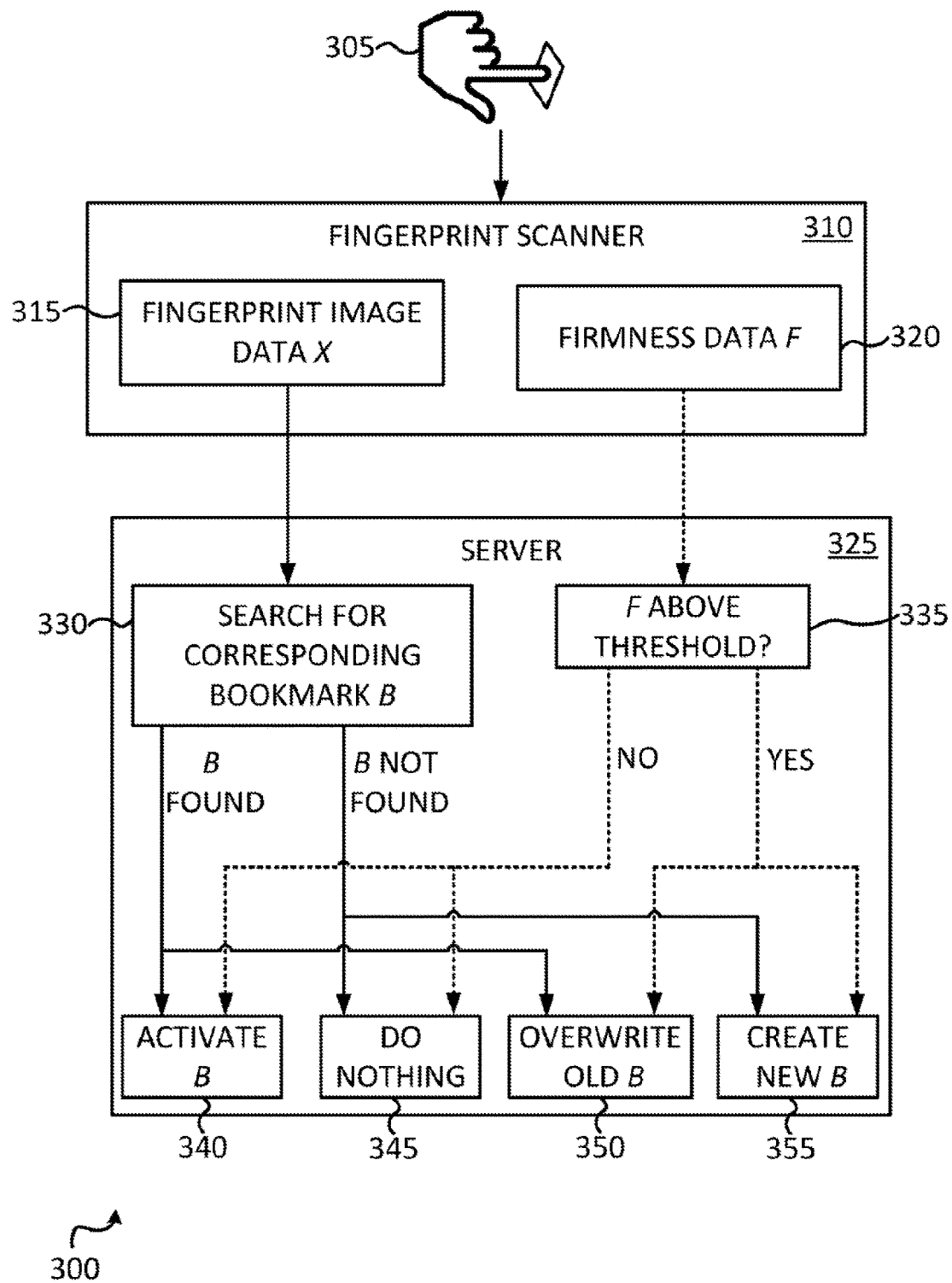
FIG. 3 shows a fingerprint bookmark system that captures firmness data, according to an exemplary embodiment of the present disclosure.

FIG. 3 shows a fingerprint bookmark system 300 that captures firmness data, according to an exemplary embodiment of the present disclosure. In some embodiments, a fingerprint scanner 310 records both a fingerprint image data 315 and a firmness data 320. Firmness data 320 may indicate a firmness value associated with how firm the contact is of user input 305 on fingerprint scanner 310. For example, the firmness value may be expressed in Newtons, the SI unit for force, or it may be expressed in kilograms*m/s$^2$, or in some other units.

In some embodiments, fingerprint bookmark system 300 may comprise a server 325 located either inside or outside the vehicle. Server 325 may comprise an operation 330 in which it is determined whether there is a stored fingerprint image within server 325 that matches fingerprint image data 315. In some embodiments, at operation 335 server 325 makes a determination as to whether firmness data 320 exceeds some firmness threshold. The firmness threshold may be set to any force value, such as 3 Newtons, 5 Newtons, or 10 Newtons. When firmness data 320 is less than the firmness threshold, it may be determined that user input 305 was a "light touch". Conversely, when firmness data 320 exceeds the firmness threshold, it may be determined that user input 305 from the vehicle occupant was a "hard touch". When firmness data 320 is equal to the firmness threshold, it may be a "light touch" or a "hard touch", depending on the embodiment. The determination at operation 335 need not necessarily be performed within server 325. Operation 335 may be performed by a processor located inside server 325, inside fingerprint scanner 310, inside the vehicle, or outside the vehicle. Operation 335 may be performed in software, or in hardware such as using a comparator circuit.

In some embodiments, fingerprint bookmark system 300 makes a determination as to which of several operations to perform. These operations include, but are not limited to: a first operation 340 to activate a found bookmark when search 330 finds a matching bookmark and firmness data 320 is less than the firmness threshold, a second operation 345 to do nothing when search 330 does not find a matching bookmark and firmness data 320 is less than the firmness threshold, a third operation 350 to overwrite the found bookmark with a new bookmark comprising the vehicle's current interior settings when search 330 finds a matching bookmark and firmness data 320 exceeds the firmness threshold, and a fourth operation 355 to create a new bookmark comprising the vehicle's current interior settings when search 330 does not find a matching bookmark and firmness data 320 exceeds the firmness threshold.

Fingerprint bookmark system 300 need not necessarily determine which of these four operations to perform within server 325. The determination may be made by a processor located inside server 325, inside fingerprint scanner 310, inside the vehicle, or outside the vehicle. The determination may be performed in software or in hardware. Similarly, operations 340, 345, 350, and 355 may be initiated by a processor located inside server 325, inside fingerprint scanner 310, inside the vehicle, or outside the vehicle. Eventually, operations 340, 345, 350, and 355 may be communicated to the one or more vehicle interior settings to which a bookmark corresponds.

Figure 4:
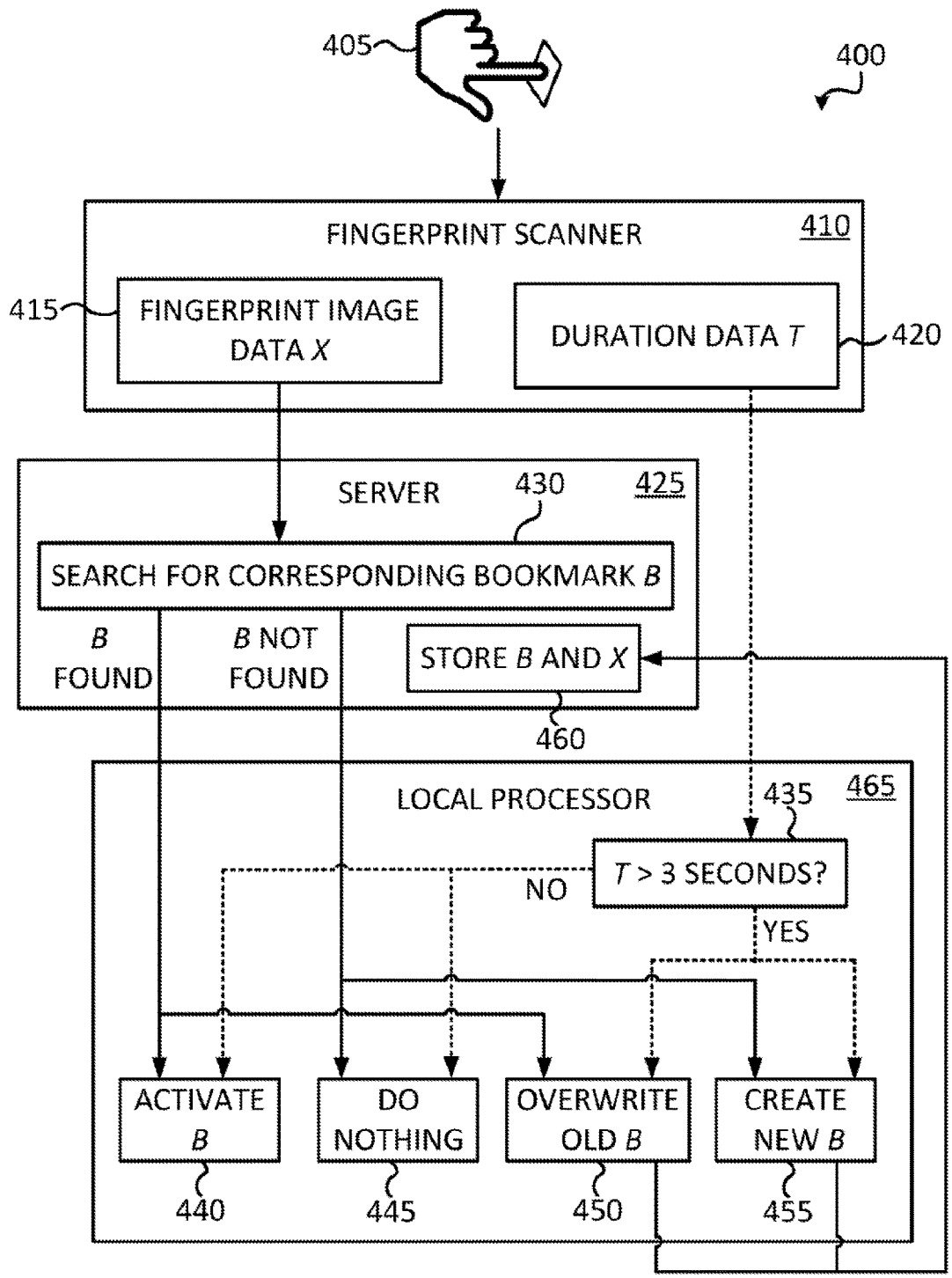
FIG. 4 shows a fingerprint bookmark system that captures duration data, according to an exemplary embodiment of the present disclosure.

FIG. 4 shows a fingerprint bookmark system 400 similar to fingerprint bookmark system 200 shown in FIG. 2, comprising a user input 405, a fingerprint scanner 410 configured to record a fingerprint image data 415 and a duration data 420, and a server 425 configured to search for a corresponding bookmark at operation 430 and store a newly created bookmark at operation 460 when a local processor 465 determines that duration data 420 exceeds the duration threshold at operation 435. Operations 440, 445, 450, and 455 may be performed within local processor 465. Both operation 450 and 455 result in fingerprint bookmark system 400 creating a new bookmark that is transmitted to server 425 for later retrieval.

Figure 5:
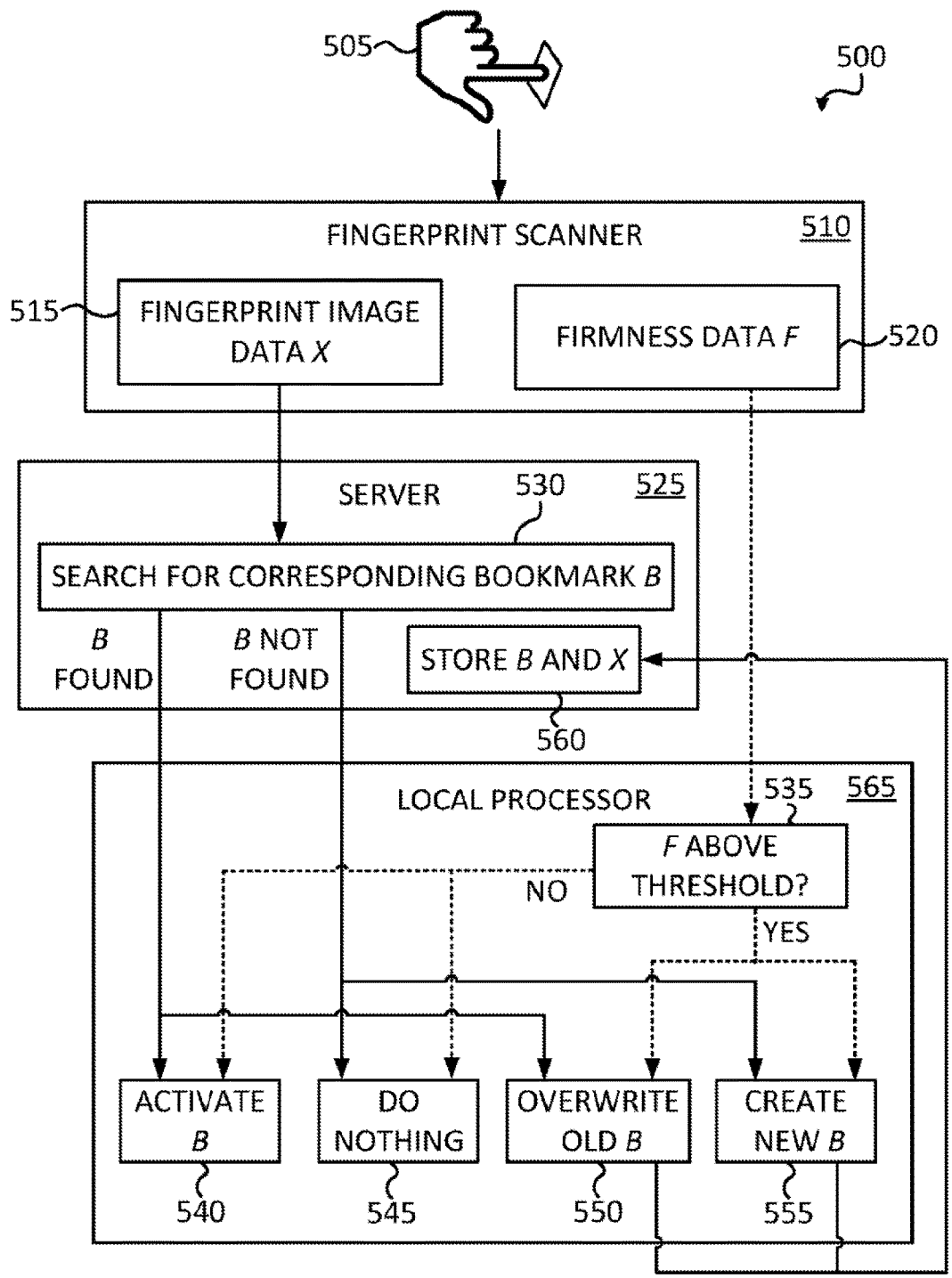
FIG. 5 shows a fingerprint bookmark system that captures firmness data, according to an exemplary embodiment of the present disclosure.

FIG. 5 shows a fingerprint bookmark system 500 similar to fingerprint bookmark system 300 shown in FIG. 3, comprising a user input 505, a fingerprint scanner 510 configured to record a fingerprint image data 515 and a firmness data 520, and a server 525 configured to search for a corresponding bookmark at operation 530 and store a newly created bookmark at operation 560 when a local processor 565 determines that firmness data 520 exceeds the firmness threshold at operation 535. Operations 540, 545, 550, and 555 may be performed within local processor 565. Both operation 550 and 555 result in fingerprint bookmark system 500 creating a new bookmark that is transmitted to server 525 for later retrieval.

Figure 6:
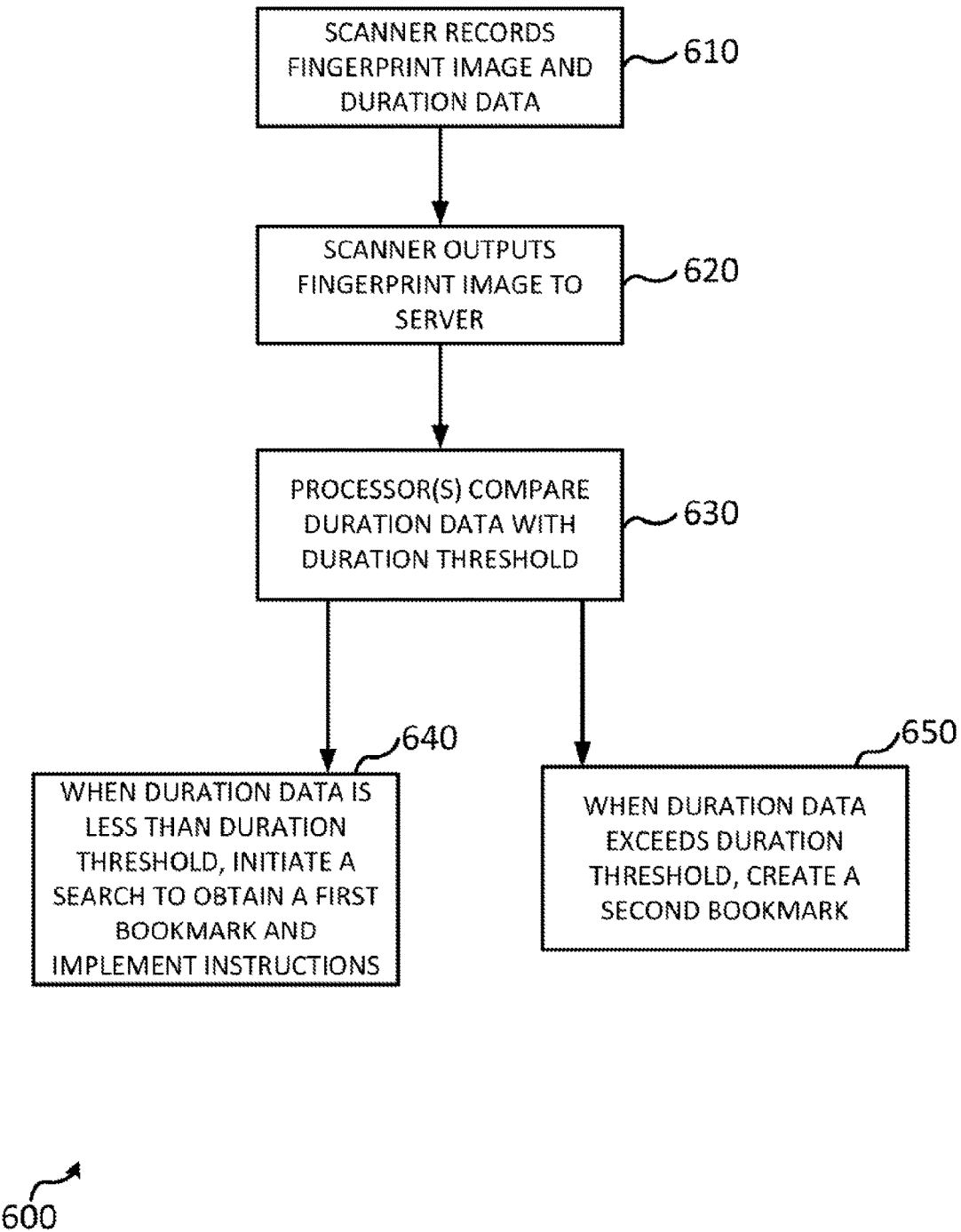
FIG. 6 shows a flow diagram of a method for modifying interior settings of a vehicle, according to an exemplary embodiment of the present disclosure.

FIG. 6 shows a method 600 for modifying interior settings of a vehicle, according to an exemplary embodiment of the present disclosure. At operation 610, a scanner records a fingerprint image and a duration data. At operation 620, a scanner outputs a fingerprint image to a server. At operation 630, one or more processors compare a duration data with a duration threshold. At operation 640, when a duration data is less than a duration threshold, a search is initiated to obtain a first bookmark and instructions contained within the first bookmark are implemented. At operation 650, when a duration data exceeds a duration threshold, a second bookmark is created.

Operations of the method 600 need not be performed in the order listed, or in any particular order. For example, in some embodiments, the comparing of a duration data with a duration threshold at operation 630 may occur before the outputting of a fingerprint image to a server at operation 620. As another example, operation 610 may be bifurcated in some embodiments. The recording of a fingerprint image at operation 610 may occur before operation 620 while the recording of a duration data at operation 610 may occur after operation 620. Furthermore, operations 640 and 650 need not both be performed each time operations 610, 620, and 630 are performed. In some embodiments, operations 640 and 650 are mutually exclusive and only one will be performed during a single iteration through method 600. In other embodiments, both operations 640 and 650 may be performed during a single iteration through method 600.

Figure 7:
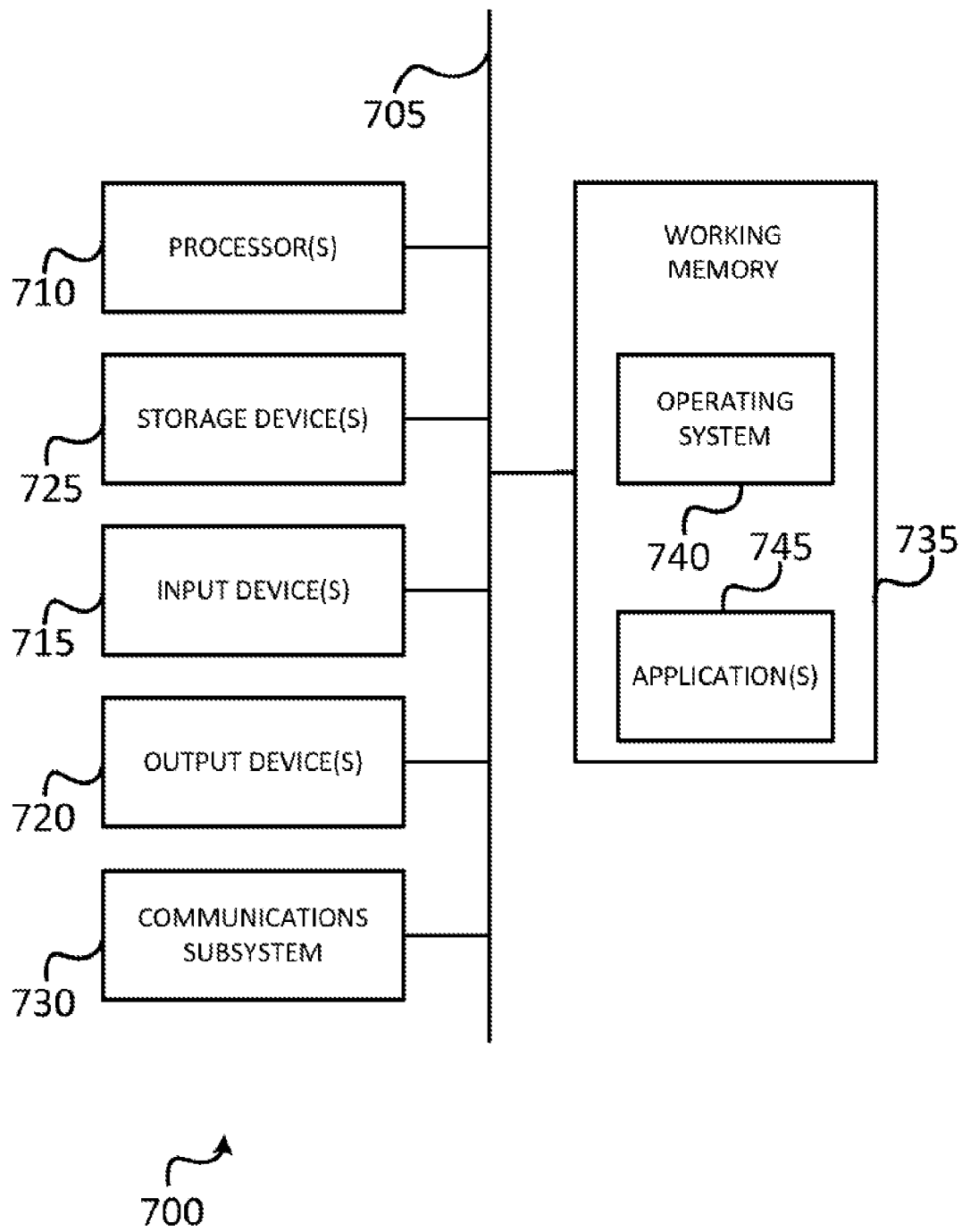
FIG. 7 shows a simplified computer system, according to an exemplary embodiment of the present disclosure.

FIG. 7 illustrates an embodiment of a computer system 700. A computer system 700 as illustrated in FIG. 7 may be incorporated into devices such as a portable electronic device, mobile phone, or other device as described herein. FIG. 7 provides a schematic illustration of one embodiment of a computer system 700 that can perform some or all of the steps of the methods provided by various embodiments. It should be noted that FIG. 7 is meant only to provide a generalized illustration of various components, any or all of which may be utilized as appropriate. FIG. 7, therefore, broadly illustrates how individual system elements may be implemented in a relatively separated or relatively more integrated manner.

The computer system 700 is shown comprising hardware elements that can be electrically coupled via a bus 705, or may otherwise be in communication, as appropriate. The hardware elements may include one or more processors 710, including without limitation one or more general-purpose processors and/or one or more special-purpose processors such as digital signal processing chips, graphics acceleration processors, and/or the like; one or more input devices 715, which can include without limitation a mouse, a keyboard, a camera, and/or the like; and one or more output devices 720, which can include without limitation a display device, a printer, and/or the like.

The computer system 700 may further include and/or be in communication with one or more non-transitory storage devices 725, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 700 might also include a communications subsystem 730, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 730 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 730. In other embodiments, a portable electronic device, e.g. the first electronic device, may be incorporated into the computer system 700, e.g., an electronic device as an input device 715. In some embodiments, the computer system 700 will further comprise a working memory 735, which can include a RAM or ROM device, as described above.

The computer system 700 also can include software elements, shown as being currently located within the working memory 735, including an operating system 740, device drivers, executable libraries, and/or other code, such as one or more application programs 745, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 7, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 725 described above. In some cases, the storage medium might be incorporated within a computer system, such as computer system 700. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 700 and/or might take the form of source and/or installable code, which, upon compilation and/or installation on the computer system 700 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 700 to perform methods in accordance with various embodiments of the technology. According to a set of embodiments, some or all of the procedures of such methods are performed by the computer system 700 in response to processor 710 executing one or more sequences of one or more instructions, which might be incorporated into the operating system 740 and/or other code, such as an application program 745, contained in the working memory 735. Such instructions may be read into the working memory 735 from another computer-readable medium, such as one or more of the storage device(s) 725. Merely by way of example, execution of the sequences of instructions contained in the working memory 735 might cause the processor(s) 710 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 700, various computer-readable media might be involved in providing instructions/code to processor(s) 710 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 725. Volatile media include, without limitation, dynamic memory, such as the working memory 735.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 710 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 700.

The communications subsystem 730 and/or components thereof generally will receive signals, and the bus 705 then might carry the signals and/or the data, instructions, etc. carried by the signals to the working memory 735, from which the processor(s) 710 retrieves and executes the instructions. The instructions received by the working memory 735 may optionally be stored on a non-transitory storage device 725 either before or after execution by the processor(s) 710.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A fingerprint bookmark system in a vehicle with one or more configurable interior settings, the fingerprint bookmark system comprising:

a scanner configured to record a fingerprint from a vehicle occupant such that a fingerprint image showing the fingerprint and firmness data for the fingerprint image are recorded by the scanner, the firmness data indicating a firmness value associated with the fingerprint image;

a remote server configured to receive the fingerprint image from the scanner and to initiate a search to obtain a first bookmark for the fingerprint shown in the fingerprint image;

a comparator circuit coupled with the scanner for determining whether the firmness data associated with the fingerprint image is less than or greater than a firmness threshold, wherein the comparator circuit is located within the vehicle; and one or more processors located within the vehicle configured to:

when the comparator circuit determines that the firmness data is less than the firmness threshold, configure an interior setting of the vehicle in accordance with one or more instructions contained in the first bookmark; and when the comparator circuit determines that the firmness data is greater than the firmness threshold, overwrite the first bookmark by replacing the first bookmark with a second bookmark for the fingerprint shown in the fingerprint image, wherein the second bookmark contains at least one instruction that is different from each of the one or more instructions contained in the first bookmark;

wherein the remote server is remote from the vehicle.

2. The vehicle fingerprint bookmark system of claim 1, wherein the firmness value is expressed in newtons.

3. A method for configuring interior settings of a vehicle, the method comprising:

recording, by a scanner, a fingerprint from a vehicle occupant such that a fingerprint image showing the fingerprint and firmness data for the fingerprint image are recorded by the scanner, the firmness data indicating a firmness value associated with the fingerprint image;

outputting, by the scanner, the fingerprint image to a remote server;

receiving, by the remote server, the fingerprint image;

initiating a search, by the remote server, to obtain a first bookmark for the fingerprint shown in the fingerprint image;

determining, by a comparator circuit coupled with the scanner, whether the firmness data associated with the fingerprint image is less than or greater than a firmness threshold, wherein the comparator circuit is located within the vehicle;

when the comparator circuit determines that the firmness data is less than the firmness threshold, configuring, by one or more processors located within the vehicle, an interior setting of the vehicle in accordance with one or more instructions contained in the first bookmark; and when the comparator circuit determines that the firmness data is greater than the firmness threshold, overwriting, by the one or more processors, the first bookmark by replacing the first bookmark with a second bookmark for the fingerprint shown in the fingerprint image, wherein the second bookmark contains at least one instruction that is different from each of the one or more instructions contained in the first bookmark;

wherein the remote server is remote from the vehicle.

4. The method of claim 3, wherein the firmness value is expressed in newtons.

5. The method of claim 3, further comprising:

performing no action when the first bookmark is not found and the firmness data is less than the firmness threshold.

* * * * *